US00PP27226P2

(12) United States Plant Patent
Horvath

(10) Patent No.: US PP27,226 P2
(45) Date of Patent: Oct. 4, 2016

(54) ***GEUM* PLANT NAMED 'SPANISH FLY'**

(50) Latin Name: ***Geum* hybrid**
Varietal Denomination: Spanish Fly

(71) Applicant: Brent Arpad Horvath, Hebron, IL (US)

(72) Inventor: Brent Arpad Horvath, Hebron, IL (US)

( * ) Notice: Subject to any disclaimer, the term of this patent is extended or adjusted under 35 U.S.C. 154(b) by 40 days.

(21) Appl. No.: 14/544,223

(22) Filed: Dec. 11, 2014

(51) Int. Cl.
*A01H 5/02* (2006.01)

(52) U.S. Cl.
USPC ..... Plt./263.1

(58) Field of Classification Search
USPC ..... Plt./263.1
CPC ..... A01H 5/02
See application file for complete search history.

(56) References Cited

PUBLICATIONS www.greenhousemag.com/article/Intrinsic-Perennial-Gardens-introductions-2014; Mar. 27, 2014; 1 page.*

* cited by examiner

*Primary Examiner* — Kent L Bell

(57) ABSTRACT

A new, distinct *Geum* plant as shown and described, characterized by ruffled single flowers RHS 16 A in color with N 34 D at the tips of the petals.

1 Drawing Sheet

Latin name: *Geum* hybrid.
Cultivar name: 'Spanish Fly'.

BACKGROUND OF THE INVENTION

The present invention relates to a new and distinct hybrid of *Geum* plant named 'Spanish Fly' characterized by ruffled single yellow-orange flowers with orange-red at the tips of the petals. The new *Geum* was the result of a breeding program in Hebron, Ill. since 2006. The new *Geum* was grown from seed collected on a group of open pollinated plants. The seed was sown in a greenhouse and the new plant was selected as a chance seedling. The selection of the new plant was made in 2010 and was due to its' ruffled single yellow-orange flowers with orange-red at the tips of the petals. The initial asexual propagation of the new *Geum* plant was by division and took place at a nursery in Hebron, Ill. since 2011. Continued asexual propagation by division since that time has shown that the unique features of the new *Geum* plant are stable and reproduced true to type in successive generations.

SUMMARY OF THE INVENTION

In the following description, color references are made to The Royal Horticultural Society Colour Chart (2001). The new *Geum* plant named 'Spanish Fly' characterized by ruffled single flowers RHS 16 A in color with N 34 D at the tips of the petals have been observed to be unique and stable.

Plants of the new *Geum* can be compared to *Geum* 'Tequila Sunrise' U.S. Plant Pat. No. 21,514, patented. 1. The new plant flower color is RHS 16 A with N 34 D at the tips of the petals while *Geum* 'Tequila Sunrise' has a bicolor flower of yellow RHS 9B blending into 46A. The new plant also has flowers that are single while *Geum* 'Tequila Sunrise' has mostly semi double flowers.

Plants of the new *Geum* can also be compared to *Geum* 'Alabama Slammer' U.S. Plant Pat. No. 23,750, patented. 1. The new plant flower color is RHS 16 A with N 34 D at the tips of the petals while *Geum* 'Alabama Slammer' has a flower color of 44 A blending into RHS N 34 A at the tips of the petals. The new plant also has flowers that are single while *Geum* 'Alabama Slammer' has mostly semi double flowers.

DESCRIPTION OF PHOTOGRAPHS

Figure 1:
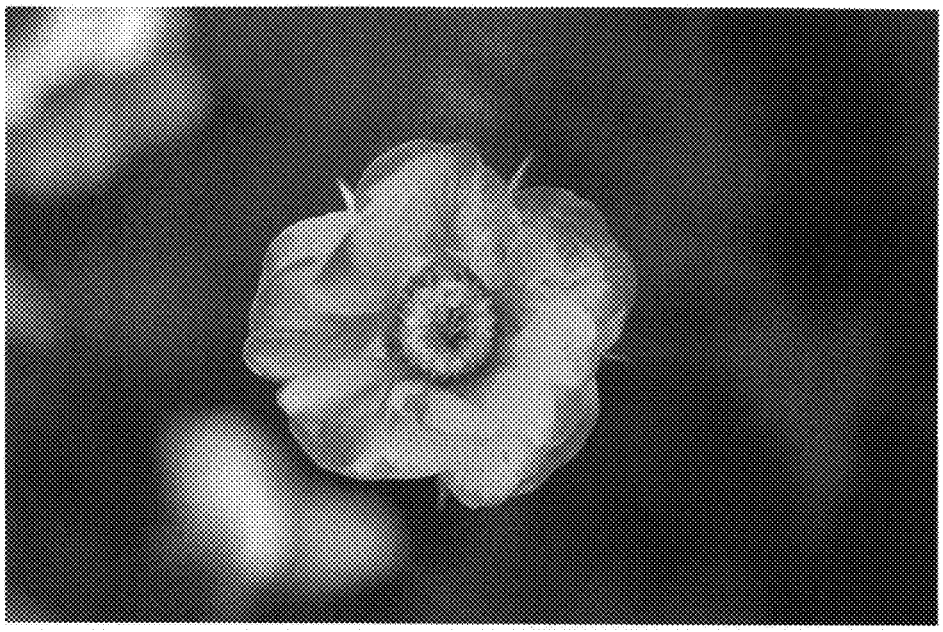
Figure 2:
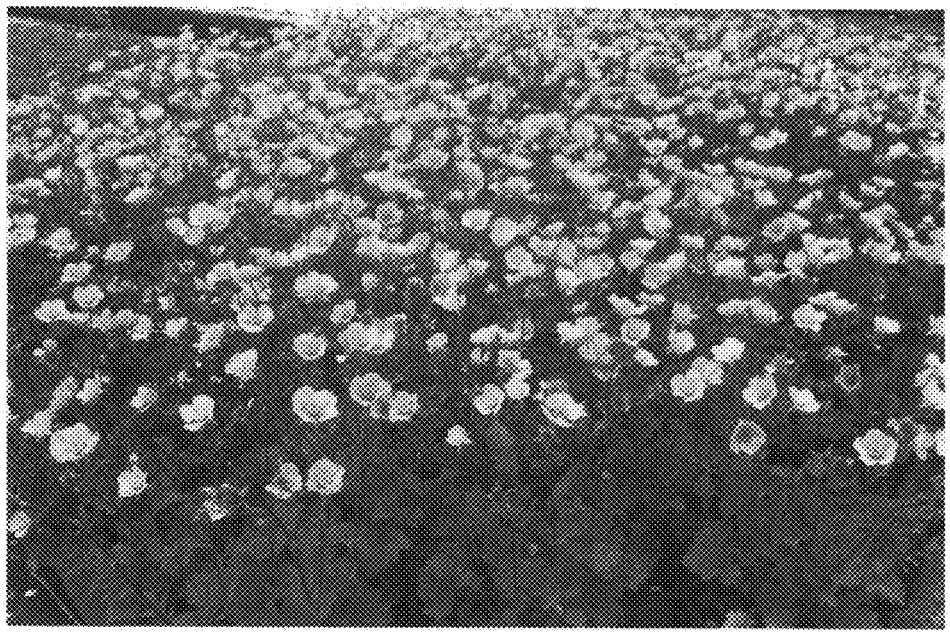

FIG. 1. Close up of the flower.
FIG. 2. Blooming plants in May.

DETAILED BOTANICAL DESCRIPTION

In the following description, color references are made to The Royal Horticultural Society Colour Chart (2001). Plants used for the description were grown in a 1 gallon container for one year at a nursery in Hebron, Ill. Measurements and numerical values represent averages of typical plants.
Botanical classification: *Geum* hybrid cultivar 'Spanish Fly'.
Parentage: Seed of open pollinated plants.
Propagation: Vegetative division.
Plant description: Overall habit of the new *Geum* is basal clumps, with upright green flower stems topped by single flowers of RHS 16 A with N 34 D at the tips of the petals.
*Plant height.*—40 cm.
*Plant width.*—35 cm.
*Stem: diameter.*—3 mm.
*Stem or basal branches.*—Length up to 40 cm, with the internodes between basal. foliage and first leaflet length being 8 cm and the second internodes between the first leaflet and the second leaflet length being 9 cm and the third internodes between the second and third leaflet length being 8 cm.
*Stem coloration.*—Of the whole stem is RHS 145 A.

Foliage description:

*Type*.—Herbaceous.

*Arrangement*.—Basal alternate with typically two or three lateral leaflets per stem.

*Petiole*.—Up to 12 cm long, with a diameter of 2 mm, color is 145 A.

*Terminal leaflet length*.—Typically 15 mm.

*Terminal leaflet width*.—Typically 10 mm.

*Terminal leaflet shape*.—Obovate with incised margins.

*Terminal and lateral leaf apex*.—Acute.

*Terminal and lateral leaf base*.—Cuneate.

*Terminal and lateral leaf margin*.—Incised.

*Texture*.—Terminal and lateral leaf, upper and lower surfaces: pubescent.

*Venation pattern*.—Terminal and lateral leaf, upper and lower surfaces: pinnate.

Venation color: Terminal and lateral leaf, upper surface is color 145 B and lower surface color is 145 C.

*Lateral leaflet number*.—2 or 3 per stem.

*Lateral leaflet length*.—4-5 cm.

*Lateral leaflet width*.—Up to 3 cm.

*Lateral leaflet shape*.—Obovate.

*Adaxial leaf description*.—Color is 145 B.

*Abaxial leaf description*.—Color 145 C.

Flower description:

*Flower type*.—Corymb.

*Adaxial flower color*.—16 A blending into tips colored N 34 D.

*Abaxial flower color*.—20 B blending into tips colored 37 A.

*Flower size*.—Diameter: 40 mm across, depth 10-15 mm.

*Flower number*.—4-5 per stem, 125 or more per plant.

*Number flowering stems*.—30.

*Bloom period and duration*.—Beginning the first week of May into the first week of June in Hebron, Ill.

*Flower longevity and duration on the plant*.—Approximately 3-4 weeks.

*Flower longevity and duration cut*.—Approximately 5-7 days.

*Scent*.—None.

*Petal count*.—10-12.

*Petal shape*.—Spathulate.

*Petal arrangement*.—Rotate, overlapping.

*Petal diameter or width*.—12 mm across and petal length- 10 mm long.

*Petal apex*.—Retuse, base: attenuate, margin: entire.

*Petal texture*.—Upper and lower surfaces: smooth, glabrous.

*Petal color*.—Upper surface is 16 A blending into tips colored N 34 D.

*Petal color*.—Lower surface color is 20 B blending into tips colored 37 A.

*Petal venation*.—Type — reniform, vein color — upper surface 16 A and sometimes N 34 D at the tips of the petals, Lower surface 20 B sometimes 37 A at the tips of the petals.

*Inflorescence diameter and height*.—14-15 cm across, 11 cm long.

*Flower buds*.—Diameter: 12 mm across, depth: 10 mm, shape: ovoid, surface: slightly pubescent and color 59A.

*Sepal size*.—Length: up to 12 mm, diameter: 6 mm at base coming to a point.

*Sepal quantity*.—6.

*Sepal shape*.—Lanceolate, apex: acute, base: cuneate, margin: entire.

*Sepal texture*.—Upper and lower surfaces: Pubescent.

*Sepal color*.—Adaxial color 59 A. Abaxial color 59 A.

*Peduncle color*.—144 B.

*Peduncle size*.—Length: 20 cm, diameter: 2 mm.

*Pedicel size*.—Length: 4-8 cm, diameter: 1-2 mm and color 144 B.

*Reproductive organs*.—Stamen — quantity over 100, length 1 cm.

*Anther*.—Quantity: over 100, length: 1 mm, diameter: close to 0.5 mm.

*Pollen*.—Typically present, color: 12A.

*Stigma*.—None observed.

*Style*.—Number: over 50, length: 6 mm.

*Pistil*.—Number: over 50, length: 6+mm.

*Ovaries*.—None observed.

*Fruit*.—None observed.

*Hardiness*.—USDA zone 4-8.

Disease resistance: Resistance to diseases common to *Geum* has not been observed on plants grown under nursery conditions.

I claim:

1. A new, distinct *Geum* plant as illustrated and described, characterized by ruffled single flowers 16 A in color with N 34 D at the tips of the petals.

* * * * *